United States Patent
Fujiki et al.

(10) Patent No.: US 11,642,433 B2
(45) Date of Patent: May 9, 2023

(54) ACTIVATED CARBON SHEET FOR AIR PURIFICATION

(71) Applicant: UNITIKA LTD., Hyogo (JP)

(72) Inventors: Hironori Fujiki, Kyoto (JP); Yoshiyuki Sometani, Kyoto (JP)

(73) Assignee: UNITIKA LTD.

( * ) Notice: Subject to any disclaimer, the term of this patent is extended or adjusted under 35 U.S.C. 154(b) by 275 days.

(21) Appl. No.: 16/967,167

(22) PCT Filed: Feb. 27, 2019

(86) PCT No.: PCT/JP2019/007416
§ 371 (c)(1),
(2) Date: Aug. 4, 2020

(87) PCT Pub. No.: WO2019/167975
PCT Pub. Date: Sep. 6, 2019

(65) Prior Publication Data
US 2020/0360559 A1   Nov. 19, 2020

(30) Foreign Application Priority Data

Feb. 28, 2018  (JP) .............................. JP2018-035424
Nov. 14, 2018  (JP) .............................. JP2018-213965
Nov. 14, 2018  (JP) .............................. JP2018-213966

(51) Int. Cl.
*A61L 9/16* (2006.01)
*C01B 32/30* (2017.01)

(52) U.S. Cl.
CPC ............. *A61L 9/16* (2013.01); *A61L 2209/21* (2013.01); *A61L 2209/22* (2013.01); *C01B 32/30* (2017.08)

(58) Field of Classification Search
CPC .... A61L 9/16; A61L 2209/21; A61L 2209/22; A61L 9/014; C01B 32/30; B01J 20/22; B01J 20/28; B60H 3/06; D21H 13/50
See application file for complete search history.

(56) References Cited

U.S. PATENT DOCUMENTS

2016/0023185 A1*  1/2016  Tabata ............... B01J 20/28011
                                              502/437
2018/0056219 A1   3/2018  Yoshida et al.

FOREIGN PATENT DOCUMENTS

CN     101337177    1/2009
CN     101468305    7/2009
(Continued)

OTHER PUBLICATIONS

Airbestpractices,"Understanding Pressure Drop" (Year: 2015).*
(Continued)

*Primary Examiner* — Sean E Conley
*Assistant Examiner* — Brendan A Hensel
(74) *Attorney, Agent, or Firm* — McDonald Hopkins LLC

(57) ABSTRACT

The present invention relates to an activated carbon sheet, and particularly relates to an activated carbon sheet for air purification comprising activated carbon, which is suitable for removing volatile organic compounds in the passenger compartment of an automobile or the like. An object of the present invention is to provide a sheet that is excellent in toluene adsorption capacity and flame retardancy. An activated carbon sheet for air purification comprising an activated carbon fiber, granular or powdered activated carbon, and a fibrillated fiber, wherein a mass (g/m²) of the activated carbon fiber is 5 g/m² or more, a pressure loss as measured by a method set forth below is 150 Pa or less, and a burn distance as measured by the FMVSS 302 burning test is 51 mm or less: <pressure loss test method> the method is conducted in accordance with JIS B 9927:1999 "Appendix (Continued)

(Standard) Cleanroom—Air filters—Test methods", 3.2 "Pressure Loss Test" as follows: a piece of the activated carbon sheet cut in the form of a circle with a diameter of 110 mm is used as a measurement sample; air is sucked though the measurement sample at a linear velocity of 0.1 m/s, and a difference in static pressure between an upstream side and a downstream side of the activated carbon sheet is measured with a differential pressure gauge; and figures up to the one's place of the measured value are used as significant figures.

14 Claims, 1 Drawing Sheet

(56) References Cited

FOREIGN PATENT DOCUMENTS

| CN | 107282003 | | | 10/2017 |
|---|---|---|---|---|
| JP | 63078739 | | | 4/1988 |
| JP | 01302627 | | | 11/1989 |
| JP | 8024637 | | | 1/1996 |
| JP | H0824637 | A | | 1/1996 |
| JP | H0824637 | A | * | 7/2000 |
| JP | 2003013390 | A | | 1/2003 |
| JP | 2003236319 | | | 8/2003 |
| JP | 2005034693 | | | 2/2005 |
| JP | 2012125717 | | | 7/2012 |
| JP | 2012125717 | A | * | 7/2012 |
| JP | 2012223662 | | | 11/2012 |
| JP | 5861450 | B2 | | 2/2016 |
| WO | 2016153062 | | | 9/2016 |

OTHER PUBLICATIONS

Chinese Office Action dated Apr. 8, 2021; Chinese Patent Application No. 201980001086.0.

Extended European Search Report dated Nov. 4, 2021; European Application No. 19761427.4.

Patent Cooperation Treaty (PCT), International Search Report and Written Opinion for Application PCT/JP2019/007416 filed on Feb. 27, 2019, dated Apr. 23, 2019, International Searching Authority, JP.

* cited by examiner (a)

(b)

ENLARGEMENT OF PITCH IN FIG. 1(a)

ACTIVATED CARBON SHEET FOR AIR PURIFICATION

CROSS-REFERENCE TO RELATED APPLICATION

This application is a 35 U.S.C. 371 national stage filing of PCT Application No. PCT/JP2019/007416, filed on Feb. 27, 2019, which claims the benefit of Japanese Patent Application No. 2018-035424 filed on Feb. 28, 2018, Japanese Patent Application No. 2018-213965 filed on Nov. 14, 2018, and Japanese Patent Application No. 2018-213966 filed on Nov. 14, 2018 each of which are incorporated herein in their entirety by reference.

TECHNICAL FIELD

The present invention relates to an activated carbon sheet, and particularly relates to an activated carbon sheet for air purification comprising activated carbon, which is suitable for removing volatile organic compounds in the passenger compartment of an automobile or the like.

BACKGROUND ART

In recent years, there has been a growing interest in air purification, and environments with reduced malodors have been required indoors or the like. Moreover, the problem of sick house syndrome has triggered a need for countermeasures against volatile organic compounds (VOCs) in residential environments.

For example, in the passenger compartment of a vehicle such as an automobile, malodors of volatile organic compounds from interior resin parts such as a seat pad, an instrument panel, and a door trim, coating materials, adhesives, and the like, as well as many malodors of exhaust gas, fuel odor, cigarettes, human bodies, rotten foods, and the like can be produced. In particular, the passenger compartment, which is a space narrower than a residence, is easily filled with such malodors when enclosed.

A deodorizing sheet for removing such malodors in a residential environment are known. For example, a deodorizing sheet is known that is manufactured by a method comprising the steps of preparing a pulp stock solution in which activated carbon, a mixed material, and a binder are homogeneously dispersed in water, and making paper therefrom to produce an activated carbon sheet; dissolving an aromatic amino acid or a salt thereof in a solvent, and attaching the aromatic amino acid or the salt thereof to the activated carbon sheet such that the attached amount thereof is in the range of 0.1 to 30% by mass by impregnating the activated carbon sheet with the solution; and drying the activated carbon sheet impregnated with the solution (see, for example, Patent Literature 1). According to Patent Literature 1, this sheet has an excellent capability of removing odors from lower aldehydes, such as acetaldehyde, and exhibits a remarkable effect of removing a sweet unpleasant odor from cigarettes, which was difficult to achieve with previous deodorizers.

CITATION LIST

Patent Literature

Patent Literature 1: JP H3-161050 A

SUMMARY OF INVENTION

Technical Problem

However, the present inventors have found that the sheet disclosed in Patent Literature 1 may be unsatisfactory in adsorption capacity of VOCs, particularly toluene. The present inventors have also found that when the sheet is used in the passenger compartment of a vehicle such as an automobile, it needs to be excellent not only in toluene adsorption capacity, but also flame retardancy. As a result of their research, however, the inventors have found that the sheet disclosed in Patent Literature 1 may have poor flame retardancy.

Accordingly, it is an object of the present invention to provide a sheet that is excellent in toluene adsorption capacity and flame retardancy, by solving the aforementioned problem.

Solution to Problem

As a result of research conducted by the present inventors to solve the aforementioned problem, they have found that the use of granular or powdered activated carbon as activated carbon is effective in achieving an excellent toluene adsorption capacity. However, the inventors have also found that when the activated carbon contained in the sheet of Patent Literature 1 is entirely composed of granular or powdered activated carbon, the resulting sheet has poor flame retardancy.

Here, based on their research, the present inventors thought that adding a halogen- or phosphorus-based flame retardant, for example, would generally improve the flame retardancy of the sheet. However, when a flame retardant is incorporated in the sheet, the mass proportion and the pore volume of the activated carbon in the sheet decrease, which reduces the toluene adsorption capacity of the sheet. That is, there is a trade-off between the toluene adsorption capacity and the flame retardancy of the sheet, i.e., an improvement in one of them causes a decrease in the other.

As a result of further research conducted by the present inventors, they have ascertained that an activated carbon fiber can impart flame retardancy, and when the activated carbon fiber is incorporated as a flame retardant component in the sheet, both toluene adsorption capacity and flame retardancy can be achieved. More specifically, the inventors have found that because an activated carbon fiber per se has toluene adsorption capacity, by incorporating the activated carbon fiber as a flame retardant component, it is possible to minimize the decrease in toluene adsorption capacity caused by the incorporation of a flame retardant component described above, thereby achieving both toluene adsorption capacity and flame retardancy. The present invention has been completed as a result of further research.

In summary, the present invention provides embodiments of the invention as itemized below:

Item 1. An activated carbon sheet for air purification comprising an activated carbon fiber, granular or powdered activated carbon, and a fibrillated fiber, wherein a mass (g/m$^2$) of the activated carbon fiber is 5 g/m$^2$ or more, a pressure loss as measured by a method set forth below is 150 Pa or less, and a burn distance as measured by the FMVSS 302 burning test is 51 mm or less:

<Pressure Loss Test Method> the method is conducted in accordance with JIS B 9927: 1999 "Appendix (Standard) Cleanroom—Air filters–Test methods", 3.2 "Pressure Loss Test" as follows: a piece of the activated carbon sheet cut in the form of a circle with a diameter of 110 mm is used as a measurement sample; air is sucked though the measurement sample at a linear velocity of 0.1 m/s, and a difference in static pressure between an upstream side and a downstream side of the activated carbon sheet is measured with a differential pressure gauge; and figures up to the one's place of the measured value are used as significant figures.

Item 2. The activated carbon sheet for air purification according to item 1, wherein an equilibrium adsorption amount of toluene at 40° C. and 1 ppm is 2000 mg/m$^2$ or more, and an equilibrium adsorption amount of acetone at 40° C. and 1 ppm is 50 mg/m$^2$ or more.

Item 3. The activated carbon sheet for air purification according to item 1 or 2, wherein a content ratio between the mass (g/m$^2$) of the activated carbon fiber and a mass (g/m$^2$) of the granular or powdered activated carbon (mass of the activated carbon fiber/mass of the granular or powdered activated carbon) is 0.05 to 0.35.

Item 4. The activated carbon sheet for air purification according to any one of items 1 to 3, wherein a content of the activated carbon fiber is 3 to 20% by mass, and a content of the granular or powdered activated carbon is 50 to 80% by mass.

Item 5. The activated carbon sheet for air purification according to any one of items 1 to 4, wherein the activated carbon fiber has a tensile strength (GPa) of 0.25 GPa or more.

Item 6. The activated carbon sheet for air purification according to any one of items 1 to 5, wherein the pressure loss is 30 to 50 Pa.

7. Use of the activated carbon sheet for air purification according to any one of items 1 to 6 for manufacturing an article for removing a volatile organic compound in the air or for removing a volatile organic compound in the air.

Item 8. A wet mixed sheet for air purification comprising an activated carbon fiber, granular or powdered activated carbon, a fibrillated fiber, a binder component, and an aldehyde adsorbent, wherein
a mass (g/m$^2$) of the activated carbon fiber is 5 g/m$^2$ or more.

Item 9. The wet mixed sheet for air purification according to any one of items 1 to 6 and 8, wherein a mass (g/m$^2$) of the granular or powdered activated carbon is 50 g/m$^2$ or more.

Item 10. The wet mixed sheet for air purification according to any one of items 1 to 6, 8, and 9, wherein a proportion of a total mass of the mass (g/m$^2$) of the activated carbon fiber and the mass (g/m$^2$) of the granular or powdered activated carbon, relative to a total of 100 parts by mass of the mass (g/m$^2$) of the activated carbon fiber, the mass (g/m$^2$) of the granular or powdered activated carbon, a mass (g/m$^2$) of the fibrillated fiber, and a mass (g/m$^2$) of the binder component, is 60 to 85 parts by mass.

Item 11. The wet mixed sheet for air purification according to any one of items 1 to 6 and 8 to 10, wherein the fibrillated fiber is non-fusible.

Item 12. The wet mixed sheet for air purification according to any one of items 1 to 6 and 8 to 11, wherein the aldehyde adsorbent is an aromatic amine compound, a cycloaliphatic amine compound, a heterocyclic amine compound, an aliphatic amine compound, or a hydrazide compound.

Item 13. The wet mixed sheet for air purification according to any one of items 1 to 6 and 8 to 12, wherein the wet mixed sheet for air purification has a specific surface area of 400 to 800 m$^2$/g.

Item 14. The wet mixed sheet for air purification according to any one of items 1 to 6 and 8 to 13, wherein the wet mixed sheet for air purification has a basis weight of 60 to 120 g/m$^2$.

Item 15. The wet mixed sheet for air purification according to any one of items 1 to 6 and 8 to 14, wherein the wet mixed sheet for air purification has a thickness of 0.2 to 0.6 mm.

Item 16. The wet mixed sheet for air purification according to any one of claims 1 to 6 and 8 to 15, wherein a burn distance as measured by the FMVSS 302 burning test is 51 mm or less.

Item 17. The wet mixed sheet for air purification according to any one of items 1 to 6 and 8 to 16, wherein an equilibrium adsorption amount of acetaldehyde at 40° C. and 1 ppm is 250 mg/m$^2$ or more, and an equilibrium adsorption amount of toluene at 40° C. and 1 ppm is 2000 mg/m$^2$ or more.

Item 18. A filter comprising a combination of a corrugated sheet and a plane sheet, wherein the corrugated sheet and the plane sheet are a mixed sheet formed of the activated carbon sheet for air purification according to any one of items 1 to 17, and a mass (g/m$^2$) of the activated carbon fiber in the mixed sheet is 5 g/m$^2$ or more.

Advantageous Effects of Invention

A sheet according to the present invention is an activated carbon sheet comprising an activated carbon fiber, granular or powdered activated carbon, and a fibrillated fiber, wherein a mass (g/m$^2$) of the activated carbon fiber is 5 g/m$^2$ or more, a pressure loss is 150 Pa or less, and a burn distance as measured by the FMVSS 302 burning test is 51 mm or less, and thereby can achieve both toluene adsorption capacity and flame retardancy. The sheet according to the present invention is thus suitable as, for example, a deodorizing sheet used in the passenger compartment of an automobile or the like, in which the flame retardancy of parts is particularly required.

DESCRIPTION OF EMBODIMENTS

An activated carbon sheet for air purification according to the present invention is an activated carbon sheet comprising an activated carbon fiber, granular or powdered activated carbon, and a fibrillated fiber. More specifically, the activated carbon sheet for air purification according to the present invention is a sheet-shaped mixture of at least an activated carbon fiber, granular or powdered activated carbon, and a fibrillated fiber. In the activated carbon sheet for air purification according to the present invention, at least the activated carbon fiber, the granular or powdered activated carbon, and the fibrillated fiber are homogeneously dispersed. In the activated carbon sheet for air purification according to the present invention, a mass (g/m$^2$) of the activated carbon fiber is 5 g/m$^2$ or more, a pressure loss as measured by a method set forth below is 150 Pa or less, and a burn distance as measured by the FMVSS 302 burning test is 51 mm or less.

<Pressure Loss Test Method>

The method is conducted in accordance with JIS (Japanese Industrial Standards) B 9927:1999 "Appendix (Standard) Cleanroom—Air filters—Test methods", 3.2 "Pressure Loss Test" as follows: a piece of the activated carbon sheet cut in the form of a circle with a diameter of 110 mm is used as a measurement sample; air is sucked though the measurement sample at a linear velocity of 0.1 m/s, and a difference in static pressure between an upstream side and a downstream side of the activated carbon sheet is measured with a differential pressure gauge; and figures up to the one's place of the measured value are used as significant figures.

More specifically, the pressure loss test is conducted as follows:

(a) Test filter material: a piece of the activated carbon sheet cut in the form of a circle with a diameter of 110 mm is used as a measurement sample.

Figure 2:
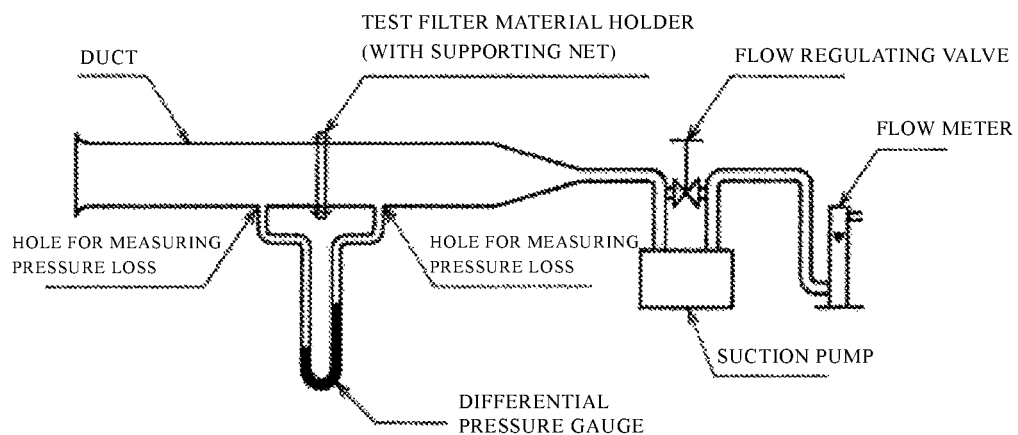
FIG. 2 is an explanatory diagram of an apparatus for measuring the pressure loss in an activated carbon sheet for air purification according to the present invention.

(b) The apparatus for measuring the pressure loss shown in FIG. 2 is used.

(c) Instruments for measuring the pressure loss are as follows:

1) Duct: a circular one having a structure such that the distribution of air velocity is as flat as possible.

2) Differential pressure gauge: one capable of reading 1 Pa.

3) Holder: one to which the test filter material as specified in (a) above can be mounted, and equipped with a supporting net for protecting the measurement sample.

4) Flow meter: one having the capabilities specified in JIS Z 8761 or JIS Z 8762.

5) Suction pump: one that provides a filtration velocity of 0.1 m/s or more.

The filtration velocity is determined based on the following equation:

$V=Q/A$, where

V: filtration velocity (cm/s);
Q: flow rate (cm$^3$/s) of filtered air; and
A: effective filtration area (cm$^2$) of the test filter material.

(d) Method for measuring the pressure loss: using the apparatus for measuring the pressure loss shown in FIG. 2, air is sucked through the test filter material at a filtration velocity that is an integral multiple of 0.1 m/s, and a difference in static pressure between an upstream side and a downstream side of the test filter material is measured. The pressure loss is calculated based on the following equation:

$\Delta P = P_1 - P_2$, where $\Delta P$: pressure loss (Pa);
$P_1$: static pressure (Pa) at the upstream side of the test filter material; and
$P_2$: static pressure (Pa) at the downstream side of the test filter material.

(e) Method for determining the pressure loss: pressure losses for three for more samples of the test filter material are measured, and the average of the measurements is determined as the pressure loss.

(f) Figures up to the one's place of the value determined by the method specified in (e) above are used as significant figures, and determined as the pressure loss in the activated carbon sheet for air purification according to the present invention.

<Activated Carbon Fiber>

The activated carbon sheet for air purification according to the present invention comprises an activated carbon fiber. In the activated carbon sheet for air purification according to the present invention, the activated carbon fiber serves as an adsorbent component for volatile organic compounds, such as toluene, and additionally serves as a flame retardant component that imparts flame retardancy to the sheet. More specifically, the activated carbon in the activated carbon fiber is a flame-resistant carbon material obtained by an infusiblization treatment and an activation treatment. Additionally, the activated carbon fiber has a bulk density considerably lower than that of granular or powdered activated carbon. It is believed that because of this low bulk density, the volume or area of the activated carbon fiber in the sheet increases, and in particular, only when the activated carbon fiber is intertwined with a fibrillated fiber or the like, i.e., a flammable component, in the form of an activated carbon sheet, so that the mass of the activated carbon fiber is 5 g/m$^2$ or more, flame retardancy can be effectively imparted to the sheet.

As the activated carbon fiber, any activated carbon fiber can be used which is manufactured by, for example, making a fiber such as a polyacrylonitrile-, rayon-, phenolic resin-, coal pitch-, or petroleum pitch-based fiber infusible, optionally subjecting the fiber to a carbonization treatment, and then activating the fiber by keeping it in an atmosphere containing steam or carbon dioxide at a predetermined temperature for a predetermined time. To further improve the flame retardancy, the coal pitch-, petroleum pitch-, or polyacrylonitrile-based activated carbon fiber is preferred among the above. A single activated carbon fiber may be used, or two or more activated carbon fibers may be used in combination. To further improve the flame retardancy of the activated carbon sheet for air purification, the carbon atom content in the activated carbon fiber is preferably 85% by mass or more, and more preferably 90% by mass or more. The oxygen atom content in the activated carbon fiber is 5% by mass or less, and particularly 3% by mass or less. Such a composition is obtained by, for example, using a raw material containing a large number of carbon atoms and a small number of oxygen atoms. The raw material is, for example, coal pitch, petroleum pitch, or polyacrylonitrile. The carbon atom content is measured using JM-11 manufactured by J-SCIENCE LAB Co., Ltd., and the oxygen atom content is measured using JMO-10 manufactured by J-SCIENCE LAB Co., Ltd.

While the strength of the activated carbon fiber is not limited, it is preferably 0.25 GPa or more, and more preferably 0.28 GPa or more. In this case, the strength of the activated carbon sheet for air purification according to the present invention can be further improved. To obtain the above-mentioned strength, an activated carbon fiber obtained by restricting the activation is preferably used; the activation may be performed to give about the below-described specific surface area, for example. The strength of the activated carbon fiber is measured and calculated in accordance with JIS K 1477:2007 7.3.2.

While the specific surface area of the activated carbon fiber is not limited, the fiber may be activated to give a specific surface area of, for example, about 500 to 1300 m$^2$/g, preferably about 500 to 900 m$^2$/g, to improve the strength of the activated carbon sheet for air purification. As used herein, the specific surface area is the value measured by the BET method (single-point method) using nitrogen as the substance to be adsorbed.

While the pore distribution of the activated carbon fiber is not limited, the micropore volume ratio is preferably 90% or more, and more preferably 95% or more, to further improve the adsorption capacity of small-molecular-size VOCs having four or less carbon atoms, for example, acetone. As used herein, the micropore volume ratio is calculated by the QSDFT method. The QSDFT (Quenched Solid Density Functional Theory) method is an analytical technique for analyzing pore sizes of geometrically and chemically disordered microporous and mesoporous carbons. This technique can calculate pore size distributions from about 0.5 nm up to about 40 nm. The QSDFT method provides a significant improvement in the accuracy of pore size distribution analysis, by explicitly taking into account the effects of pore surface roughness and heterogeneity. Herein, nitrogen adsorption isotherm measurement is performed using "AUTOSORB-1-MP" manufactured by Quantachrome, and pore size distribution analysis is performed using the QSDFT method. Pore volumes in a specific range of pore sizes can be calculated by calculating a pore size distribution by applying the calculation model, $N_2$ at 77K on carbon [slit pore, QSDFT equilibrium model], to a nitrogen desorption isotherm measured at a temperature of 77 K. Then, based on the total pore volume measured and calculated using the QSDFT method, and the pore volume of pores with a diameter of 2 nm or less measured and calculated using the QSDFT method, the micropore volume ratio is determined according to the following equation:

Micropore volume ratio (%)=(pore volume of pores with a diameter of 2 nm or less)/(total pore volume)×100(%)

While the average fiber diameter of the activated carbon fiber is not limited, it is preferably 15 to 25 μm, more preferably 16 to 20 μm, and still more preferably 16.5 to 20 μm, to improve the strength of the activated carbon sheet for air purification. The average fiber diameter is measured and calculated using a reflection microscope, in accordance with JIS K 1477:2007 7.3.1.

In the activated carbon sheet for air purification according to the present invention, the mass of the activated carbon fiber is 5 g/m² or more. During research on the present invention, the present inventors compared a sheet in which the mass of the activated carbon fiber was 6 g/m² and the sheet basis weight was 20 g/m² (remainder: polyester fiber) and a sheet in which the mass of the activated carbon fiber was 14 g/m² and the sheet basis weight was 50 g/m² (remainder: polyester fiber), in terms of flame retardancy. The mixed ratio of the activated carbon fiber was similar in both sheets, whereas the amount of the relatively flammable polyester fiber was greater in the latter sheet; however, the latter sheet was superior in flame retardancy. Based on the above as well as the Examples shown below and the like, the present inventors have found that the mass per unit area (g/m²) of the activated carbon fiber is important for the flame retardancy of the sheet. As a result of their further research, the present inventors have found that because of a low bulk density of the activated carbon fiber, the volume or area of the activated carbon fiber in the sheet increases, and in particular, it is important to incorporate the specific amount of the activated carbon fiber while intertwining the activated carbon fiber with a fibrillated fiber or the like, i.e., a flammable component, in the form of an activated carbon sheet. To further improve the flame retardancy, the mass of the activated carbon fiber is preferably 9 g/m² or more. To more satisfactorily achieve both toluene adsorption capacity and flame retardancy, the mass of the activated carbon fiber is preferably 9 to 20 g/m², and more preferably 13 to 18 g/m².

In the activated carbon sheet for air purification according to the present invention, the content ratio between the mass (g/m²) of the activated carbon fiber and the mass (g/m²) of the below-described granular or powdered activated carbon (mass of the activated carbon fiber/mass of the granular or powdered activated carbon) is preferably 0.05 to 0.35. By blending the activated carbon fiber, which serves as a flame retardant component and a toluene adsorbent component, and the granular or powdered activated carbon, which serves as a toluene adsorbent component, to give the specific ratio, the resulting activated carbon sheet for air purification can achieve both toluene adsorption capacity and flame retardancy. The above-mentioned ratio is more preferably 0.15 to 0.30, and more preferably 0.25 to 0.30.

In the activated carbon sheet for air purification according to the present invention, the proportion of the mass (g/m²) of the activated carbon fiber, relative to a total of 100 parts by mass of the mass (g/m²) of the activated carbon fiber, the mass (g/m²) of the granular or powdered activated carbon, and the mass (g/m²) of the fibrillated fiber, is 3 to 20 parts by mass, for example. To more satisfactorily achieve both toluene adsorption capacity and flame retardancy, the above-mentioned proportion is preferably 10 to 20 parts by mass, and more preferably 14 to 18 parts by mass. The proportion of the mass (g/m²) of the activated carbon fiber relative to the mass (g/m²) of the activated carbon sheet for air purification according to the present invention is 3 to 25% by mass. To more satisfactorily achieve both toluene adsorption capacity and flame retardancy, the above-mentioned proportion is preferably 3 to 20% by mass, more preferably 8 to 20% by mass, and still more preferably 13 to 18% by mass.

When a wet mixed sheet for air purification according to the present invention comprises a binder component, the proportion of the mass (g/m²) of the activated carbon fiber relative to a total of 100 parts by mass of the mass (g/m²) of the activated carbon fiber, the mass (g/m²) of the granular or powdered activated carbon, the mass (g/m²) of the fibrillated fiber, and the mass (g/m²) of the binder component, is 3 to 25 parts by mass, for example. To more satisfactorily achieve both toluene adsorption capacity and flame retardancy, the above-mentioned proportion is preferably 8 to 20 parts by mass, and more preferably 13 to 18 parts by mass. The proportion of the mass (g/m²) of the activated carbon fiber relative to the mass (g/m²) of the wet mixed sheet for air purification according to the present invention is 3 to 25% by mass. To more satisfactorily achieve both toluene adsorption capacity and flame retardancy, the above-mentioned proportion is preferably 8 to 20% by mass, and more preferably 13 to 18% by mass.

<Granular or Powdered Activated Carbon>

The activated carbon sheet for air purification according to the present invention comprises granular or powdered activated carbon. The granular or powdered activated carbon in the activated carbon sheet for air purification according to the present invention serves as an adsorbent component for volatile organic compounds, such as toluene.

Examples of the granular or powdered activated carbon include known activated carbons, such as coconut shell activated carbon made from coconut shells, coal-based activated carbon made from coal, wood-based activated carbon made from wood, and resin-based activated carbon made from a resin such as phenolic resin. A single powdered activated carbon may be used, or two or more powdered activated carbons may be used in combination.

While the average particle diameter of the granular or powdered activated carbon is not limited, the cumulative volume percentage $D_{50}$ measured by the laser diffraction/scattering method is 10 to 150 μm, preferably 10 to 100 μm, and more preferably 10 to 50 μm, to achieve the ease of making paper and prevent coal dust from falling off.

The specific surface area of the granular or powdered activated carbon is, for example, 500 to 1500 $m^2/g$, and preferably 600 to 1300 $m^2/g$.

In the activated carbon sheet for air purification according to the present invention, the mass ($g/m^2$) of the granular or powdered activated carbon is preferably 50 $g/m^2$ or more. In this case, the toluene adsorption capacity is likely to be further improved. To more satisfactorily achieve both toluene adsorption capacity and flame retardancy, the mass ($g/m^2$) of the granular or powdered activated carbon is more preferably 50 to 70 $g/m^2$, and still more preferably 50 to 60 $g/m^2$.

In the activated carbon sheet for air purification according to the present invention, the proportion of the mass ($g/m^2$) of the granular or powdered activated carbon, relative to a total of 100 parts by mass of the mass ($g/m^2$) of the activated carbon fiber, the mass ($g/m^2$) of the granular or powdered activated carbon, and the mass ($g/m^2$) of the fibrillated fiber, is 50 to 80 parts by mass, for example. To more satisfactorily achieve both toluene adsorption capacity and flame retardancy, the above-mentioned proportion is preferably 55 to 68 parts by mass, and more preferably 58 to 63 parts by mass. The proportion of the mass ($g/m^2$) of the granular or powdered activated carbon relative to the mass ($g/m^2$) of the activated carbon sheet for air purification according to the present invention is, for example, 45 to 75% by mass. To more satisfactorily achieve both toluene adsorption capacity and flame retardancy, the above-mentioned proportion is preferably 45 to 62% by mass, and more preferably 50 to 57% by mass.

When the wet mixed sheet for air purification according to the present invention comprises a binder component, the proportion of the mass ($g/m^2$) of the granular or powdered activated carbon relative to a total of 100 parts by mass of the mass ($g/m^2$) of the activated carbon fiber, the mass ($g/m^2$) of the granular or powdered activated carbon, the mass ($g/m^2$) of the fibrillated fiber, and the mass ($g/m^2$) of the binder component, is 45 to 75 parts by mass, for example. To more satisfactorily achieve both toluene adsorption capacity and flame retardancy, the above-mentioned proportion is preferably 45 to 62 parts by mass, and more preferably 50 to 57 parts by mass. The proportion of the mass ($g/m^2$) of the granular or powdered activated carbon relative to the mass ($g/m^2$) of the wet mixed sheet for air purification according to the present invention is, for example, 45 to 75% by mass. To more satisfactorily achieve both toluene adsorption capacity and flame retardancy, the above-mentioned proportion is preferably 45 to 62% by mass, and more preferably 50 to 57% by mass.

<Fibrillated Fiber>

The activated carbon sheet for air purification according to the present invention comprises a fibrillated fiber. In the activated carbon sheet for air purification according to the present invention, the fibrillated fiber serves to retain the form of the activated carbon sheet for air purification, and retain the granular or powdered activated carbon.

To further improve the toluene adsorption capacity, the fibrillated fiber is preferably a non-fusible fibrillated fiber. Examples include acrylic fibers, polyethylene fibers, polyacrylonitrile fibers, cellulose fibers, and aramid fibers. To further improve the flame retardancy, an aramid fiber is preferred among the above.

The freeness of the fibrillated fiber is preferably such that the freeness measured in accordance with JIS P 8121-2:2012 is 10 to 200 mL.

In the activated carbon sheet for air purification according to the present invention, the proportion of the mass ($g/m^2$) of the fibrillated fiber, relative to a total of 100 parts by mass of the mass ($g/m^2$) of the activated carbon fiber, the mass ($g/m^2$) of the granular or powdered activated carbon, and the mass ($g/m^2$) of the fibrillated fiber, is 10 to 30 parts by mass, for example. To more satisfactorily achieve both toluene adsorption capacity and flame retardancy, the above-mentioned proportion is preferably 15 to 30 parts by mass, and more preferably 18 to 25 parts by mass. The proportion of the fibrillated fiber relative to the mass ($g/m^2$) of the activated carbon sheet for air purification according to the present invention is 10 to 30% by mass, for example. To more satisfactorily achieve both toluene adsorption capacity and flame retardancy, the above-mentioned proportion is preferably 18 to 27% by mass, and more preferably 18 to 22% by mass.

When the wet mixed sheet for air purification according to the present invention comprises a binder component, the proportion of the mass ($g/m^2$) of the fibrillated fiber relative to a total of 100 parts by mass of the mass ($g/m^2$) of the activated carbon fiber, the mass ($g/m^2$) of the granular or powdered activated carbon, the mass ($g/m^2$) of the fibrillated fiber, and the mass ($g/m^2$) of the binder component, is 10 to 30 parts by mass, for example. The above-mentioned proportion is preferably 18 to 27 parts by mass to more satisfactorily achieve both toluene adsorption capacity and flame retardancy, and is more preferably 18 to 22 parts by mass to further inhibit dusting of the granular or powdered activated carbon. The proportion of the fibrillated fiber relative to the mass ($g/m^2$) of the wet mixed sheet for air purification according to the present invention is 10 to 30% by mass, for example. To more satisfactorily achieve both toluene adsorption capacity and flame retardancy, the above-mentioned proportion is preferably 18 to 27% by mass, and more preferably 18 to 22% by mass.

<Binder Component>

The activated carbon sheet for air purification according to the present invention can optionally comprise a binder component. In the activated carbon sheet for air purification according to the present invention, the binder component is a component that bonds and fixes the activated carbon fiber, the granular or powdered activated carbon, and the fibrillated fiber, and serves to retain the form of the activated carbon sheet for air purification, and retain the granular or powdered activated carbon.

Examples of the binder component include organic or inorganic binders having adhesive properties (including thermally fusible properties). The binder may be in the form of a powder, granules, a fiber, or the like, although the form is not limited thereto. As used herein, the binder component is defined as not including the fibrillated fiber described above.

Examples of organic binders include synthetic resins, for example, thermoplastic resins, such as polyvinyl alcohol, acrylic resins, modified polyesters (so-called low-softening-point polyesters), polyolefins (PE, PP, and the like), and ethylene-vinyl acetate copolymer (EVA). When a thermally fusible fiber is used as the binder component, the thermally fusible fiber is preferably a fiber formed of two or more polymer components having different melting points or softening points. The thermally fusible fiber is particularly preferably a fiber having a sheath-core structure in which a high-melting-point polymer is used as a core component and a low-melting-point polymer as a sheath component, to facilitate the heat treatment in the formation of the sheet. Examples of fibers having such a sheath-core structure include composite fibers, for example, polyolefin-based fibers in which polypropylene is used as the core and modified polyethylene as the sheath; fibers in which polyethylene terephthalate is used as the core and a polyolefin as the sheath; and polyester-based fibers in which polyethylene terephthalate is used as the core and a low-melting-point (low-softening-point) polyester as the sheath.

Examples of inorganic binders include colloidal silica, water glass, calcium silicate, alumina sol, silicone oils, and metal alkoxides.

Among the above, polyvinyl alcohol is preferred to further inhibit dusting of the granular or powdered activated carbon in the activated carbon sheet for air purification.

The proportion of the binder component relative to the mass $(g/m^2)$ of the activated carbon sheet for air purification according to the present invention is, for example, 3 to 15% by mass, preferably 3 to 13% by mass to more satisfactorily achieve both toluene adsorption capacity and flame retardancy, and more preferably 8 to 13% by mass to further inhibit dusting of the granular or powdered activated carbon.

When the wet mixed sheet for air purification according to the present invention comprises a binder component, the proportion of the mass $(g/m^2)$ of the binder component relative to a total of 100 parts by mass of the mass $(g/m^2)$ of the activated carbon fiber, the mass $(g/m^2)$ of the granular or powdered activated carbon, the mass $(g/m^2)$ of the fibrillated fiber, and the mass $(g/m^2)$ of the binder component, is, for example, 3 to 15 parts by mass, preferably 3 to 13 parts by mass to more satisfactorily achieve both toluene adsorption capacity and flame retardancy, and more preferably 8 to 13 parts by mass to further inhibit dusting of the granular or powdered activated carbon. The proportion of the binder component relative to the mass $(g/m^2)$ of the wet mixed sheet for air purification according to the present invention is, for example, 3 to 15% by mass, preferably 3 to 13% by mass to more satisfactorily achieve both toluene adsorption capacity and flame retardancy, and more preferably 8 to 13% by mass to further inhibit dusting of the granular or powdered activated carbon.

<Aldehyde Adsorbent>

The activated carbon sheet for air purification according to the present invention can comprise an aldehyde adsorbent. In this case, the activated carbon sheet for air purification according to the present invention can adsorb an aldehyde component, for example, acetaldehyde.

The aldehyde adsorbent is preferably an aromatic amine compound, a cycloaliphatic amine compound, a heterocyclic amine compound, or an aliphatic amine compound.

Examples of aromatic amine compounds include aromatic amino acids such as o-, m- or p-aminobenzoic acid, p-aminosalicylic acid, and m-aminosalicylic acid, sulfanilic acid, aniline, anisidine, and metal salts thereof such as sodium salt and potassium salt, or inorganic salts thereof such as sulfate, nitrate, and hydrochloride.

Examples of cycloaliphatic amine compounds include cyclopropylamine, cyclobutylamine, cyclopentylamine, and cyclohexylamine.

Examples of heterocyclic amine compounds include pyrrolidine, piperidine, piperazine, morpholine, oxazine, quinuclidine, pyrrole, pyrazole, imidazole, pyridine, pyridazine, pyrimidine, pyrazine, oxazol, thiazole, 4-dimethylaminopyridine, 1,4-diazabicyclo[2,2,2]octane, 1,5-diazabicyclo[4,3,0]-5-nonene, and 1,8-diazabicyclo[5,4,0]-7-undecene.

Examples of aliphatic amine compounds include methylamine, ethylamine, propylamine, isopropylamine, butylamine, amylamine, hexylamine, heptylamine, octylamine, nonylamine, decylamine, undecylamine, dodecylamine, tridecylamine, tetradecylamine, pentadecylamine, cetylamine, tetraethylenepentamine, diethylenetriamine, arginine, ethanolamine, guanidine, and polyethyleneimine.

Examples of hydrazide compounds include adipic dihydrazide, succinic dihydrazide, sebacic dihydrazide, and carbodihydrazide.

Among the above, an aromatic amine compound or a heterocyclic amine is preferred, and p-aminobenzoic acid or morpholine is particularly preferred.

The manner in which the aldehyde adsorbent is incorporated in the activated carbon sheet for air purification according to the present invention is not limited. Examples of methods include a method in which an activated carbon sheet containing an activated carbon fiber, granular or powdered activated carbon, a fibrillated fiber, and optionally a binder component is manufactured in advance, and a solution in which an aldehyde adsorbent is dispersed is impregnated into or sprayed to the sheet to incorporate the aldehyde adsorbent in the sheet; and a method in which an aldehyde adsorbent is incorporated in advance in one or more constituent materials selected from the group consisting of an activated carbon fiber, granular or powdered activated carbon, a fibrillated fiber, and optionally a binder component, and an activated carbon sheet is manufactured using the constituent materials. In particular, it is preferred to incorporate an aldehyde adsorbent in the granular or powdered activated carbon in advance to obtain an activated carbon sheet; more specifically, it is preferred to obtain an activated carbon sheet for air purification containing an activated carbon fiber, granular or powdered activated carbon, a fibrillated fiber, an aldehyde adsorbent, and optionally a binder component, in which the aldehyde adsorbent is supported on the granular or powdered activated carbon, and an aldehyde adsorbent is not supported on the activated carbon fiber. In this case, because an aldehyde adsorbent, which is an organic substance, is not supported on the activated carbon fiber that serves as a flame retardant material, the capability of the activated carbon fiber as a flame retardant material can more readily demonstrated.

The content of the aldehyde adsorbent may be appropriately determined according to the required capability; for example, when the aldehyde adsorbent is supported on the granular or powdered activated carbon, the content of the aldehyde adsorbent is 1 to 50 parts by mass, and preferably 5 to 20% by weight, relative to 100 parts by mass of the granular or powdered activated carbon (before the aldehyde adsorbent is supported thereon). The content of the aldehyde adsorbent in the activated carbon sheet for air purification is 0.1 to 35% by mass, and particularly 1 to 15% by mass.

<Other Components>

The activated carbon sheet for air purification according to the present invention can optionally contain other components besides the activated carbon fiber, the granular or powdered activated carbon, the fibrillated fiber, the binder component, and the aldehyde adsorbent.

Examples of the other components include a flame retardant excluding activated carbon fibers. Examples of preferred flame retardants include aluminum hydroxide, which has little impact on the human body and the environment, and is less likely to coat activated carbon. The content of the flame retardant in the activated carbon sheet for air purification according to the present invention is 3 to 10% by mass, for example.

<Physical Properties of the Activated Carbon Sheet for Air Purification According to the Present Invention>

1. Pressure Loss

In the activated carbon sheet for air purification according to the present invention, the pressure loss as measured by the method set forth below is 150 Pa or less. Because of this, the activated carbon sheet for air purification according to the present invention can be suitably used as an activated carbon sheet for air purification. To more satisfactorily achieve both the ease of air flow and toluene adsorption capacity, the pressure loss is preferably 10 to 80 Pa, and more preferably 20 to 60 Pa.

<Pressure Loss Test Method>

The method is conducted in accordance with JIS B 9927:1999 "Appendix (Standard) Cleanroom—Air filters—Test methods", 3.2 "Pressure Loss Test" as follows: a piece of the activated carbon sheet cut in the form of a circle with a diameter of 110 mm is used as a measurement sample; air is sucked though the measurement sample at a linear velocity of 0.1 m/s, and a difference in static pressure between an upstream side and a downstream side of the activated carbon sheet is measured with a differential pressure gauge; and figures up to the one's place of the measured value are used as significant figures.

2. Flame Retardancy

The activated carbon sheet for air purification according to the present invention has excellent flame retardancy because it comprises an activated carbon fiber, granular or powdered activated carbon, and a fibrillated fiber, wherein a content ratio between the mass ($g/m^2$) of the activated carbon fiber and the mass ($g/m^2$) of the granular or powdered activated carbon (mass of the activated carbon fiber/mass of the granular or powdered activated carbon) is 0.05 to 0.35. The flame retardancy of the activated carbon sheet for air purification according to the present invention is such that a burn distance as measured by the FMVSS 302 burning test is 51 mm or less, preferably 10 mm or less, and more preferably 5 mm or less.

3. Specific Surface Area ($m^2/g$)

The activated carbon sheet for air purification according to the present invention preferably has a specific surface area of 400 to 800 $m^2/g$, more preferably 500 to 650 $m^2/g$, and still more preferably 550 to 650 $m^2/g$. As used herein, the specific surface area of the activated carbon sheet for air purification according to the present invention is the value measured by the BET method (single-point method) using nitrogen as the substance to be adsorbed.

4. Basis Weight ($g/m^2$) and Thickness (mm)

The activated carbon sheet for air purification according to the present invention preferably has a basis weight of 60 to 120 $g/m^2$, and more preferably 75 to 105 $g/m^2$. Moreover, the activated carbon sheet for air purification according to the present invention preferably has a thickness of 0.2 to 0.6 mm, and more preferably 0.3 to 0.4 mm. As used herein, the basis weight of the activated carbon sheet for air purification is the mass ($g/m^2$) per unit area measured in accordance with JIS L 1913:2010 6.2. As used herein, the thickness of the activated carbon sheet for air purification is the thickness (mm) of the sheet determined by making three-point measurements at given places using a thickness gauge manufactured by Mitutoyo Corporation, and calculating the average of the measured values.

5. Toluene Adsorption Capacity

The activated carbon sheet for air purification according to the present invention has an excellent toluene adsorption capacity because it comprises an activated carbon fiber, granular or powdered activated carbon, and a fibrillated fiber, wherein the mass ($g/m^2$) of the activated carbon fiber is 5 $g/m^2$ or more. The toluene adsorption capacity of the activated carbon sheet for air purification according to the present invention is such that the equilibrium adsorption amount at an equilibrium concentration of 1 ppm and 40° C. is preferably 2000 $mg/m^2$ or more, and more preferably 3000 $mg/m^2$ or more. The toluene adsorption capacity is measured and calculated as follows: A sample having a given area and 3 L of 100-ppm toluene gas are sealed in a hermetically sealed container, and allowed to stand in an environment at a room temperature of 40° C. After a lapse of 24 hours, the gas concentration in the container is measured, and the gas adsorption amount by the sample is calculated based on the amount of decrease in the concentration. The measurement is conducted for a plurality of sample areas, and based on the results of calculation, the correlation between concentration and adsorption amount is plotted on a graph. From the relation thus obtained, the equilibrium adsorption amount ($mg/m^2$) of toluene at an equilibrium concentration of 1 ppm is derived. The toluene concentration is measured using gas chromatography. While the upper limit of the toluene adsorption capacity is not limited, it is, for example, 5000 $mg/m^2$ or less.

6. Acetone Adsorption Capacity

By using activated carbon having a high micropore volume ratio, the activated carbon sheet for air purification according to the present invention can have an improved acetone adsorption capacity. The acetone adsorption capacity of the activated carbon sheet for air purification according to the present invention is such that the equilibrium adsorption amount at an equilibrium concentration of 1 ppm and 40° C. is preferably 50 $mg/m^2$ or more, and more preferably 65 $mg/m^2$ or more. The acetone adsorption capacity is measured and calculated as follows: A sample having a given area and 3 L of 100-ppm acetone gas are sealed in a hermetically sealed container, and allowed to stand in an environment at a room temperature of 40° C. After a lapse of 24 hours, the gas concentration in the container is measured, and the gas adsorption amount by the sample is calculated based on the amount of decrease in the concentration. The measurement is conducted for a plurality of sample areas, and based on the results of calculation, the correlation between concentration and adsorption amount is plotted on a graph. From the relation thus obtained, the equilibrium adsorption amount ($mg/m^2$) of acetone at a given equilibrium concentration of 1 ppm is derived. The acetone concentration is measured using gas chromatography. While the upper limit of the acetone adsorption capacity is not limited, it is, for example, 300 $mg/m^2$ or less.

7. Aldehyde Adsorption Capacity

By incorporation of an aldehyde adsorbent, the activated carbon sheet for air purification according to the present invention can have an excellent aldehyde adsorption capacity. In this case, the acetaldehyde adsorption capacity of the activated carbon sheet for air purification according to the present invention is such that the equilibrium adsorption amount at an equilibrium concentration of 1 ppm and 40° C. is preferably 250 $mg/m^2$ or more, and more preferably 300 $mg/m^2$ or more. The aldehyde adsorption capacity is measured and calculated as follows: A sample having a given area and 3 L of 100-ppm acetaldehyde gas are sealed in a hermetically sealed container, and allowed to stand in an environment at a room temperature of 40° C. After a lapse of 24 hours, the gas concentration in the container is measured, and the gas adsorption amount by the sample is calculated based on the amount of decrease in the concentration. The measurement is conducted for a plurality of sample areas, and based on the results of calculation, the correlation between concentration and adsorption amount is plotted on a graph. From the relation thus obtained, the equilibrium adsorption amount ($mg/m^2$) of acetaldehyde at a given equilibrium concentration of 1 ppm is derived. The acetaldehyde concentration is measured using gas chromatography. While the upper limit of the acetaldehyde adsorption capacity is not limited, it is, for example, 700 $mg/m^2$ or less.

<Method for Manufacturing the Activated Carbon Sheet for Air Purification According to the Present Invention>

While the method for manufacturing the activated carbon sheet for air purification is not limited, the activated carbon sheet for air purification can be manufactured by, for example, making paper from a mixture of the activated carbon fiber, the granular or powdered activated carbon, the fibrillated fiber, and optionally the binder component, by a wet paper-making method. Specifically, the activated carbon fiber, the granular or powdered activated carbon, the fibrillated fiber, and optionally the binder component are mixed and sheared using an apparatus such as a pulper, a beater, or a refiner, to prepare a slurry in which these components are homogeneously dispersed, and the slurry is passed onto wires at a predetermined flow rate and dehydrated to adjust the basis weight to a given value. The sheet thereafter undergoes a press part, a dryer part where the sheet is dried, and a calender part where the sheet surface is smoothened, and then the sheet is wound up onto a reel. Using such a known technique, for example, the sheet can be manufactured. The thickness of the sheet may be adjusted to a given thickness, using a heat press roller or the like. When an aldehyde adsorbent is to be incorporated, examples therefor include a method in which the aldehyde adsorbent is incorporated into the slurry; a method in which the aldehyde adsorbent is incorporated into the sheet by, for example, spraying or impregnation, after the sheet is manufactured; and a method in which the aldehyde adsorbent is incorporated into the activated carbon fiber or the granular or powdered activated carbon in advance. In particular, in order to obtain a more preferred embodiment of the activated carbon sheet for air purification according to the present invention, i.e., to obtain an activated carbon sheet for air purification containing an activated carbon fiber, granular or powdered activated carbon, a fibrillated fiber, an aldehyde adsorbent, and optionally a binder component, in which the aldehyde adsorbent is supported on the granular or powdered activated carbon, and an aldehyde adsorbent is not supported on the activated carbon fiber, it is preferred to prepare granular or powdered activated carbon on which an aldehyde adsorbent is supported, an activated carbon fiber on which an aldehyde adsorbent is not supported, a fibrillated fiber, and optionally a binder component, and manufacture a sheet from these raw materials by a wet paper-making method.

<Applications of the Activated Carbon Sheet for Air Purification According to the Present Invention>

The activated carbon sheet for air purification according to the present invention can be used as a sheet for air purification, particularly a sheet for removing toluene in an indoor space. The activated carbon sheet for air purification according to the present invention can also be used for manufacturing an article for removing a volatile organic compound in the air or for removing a volatile organic compound in the air. The volatile organic compound refers to an organic compound that is gaseous in the atmosphere at 1 atm and 25° C. The volatile organic compound is, for example, one or more selected from the group consisting of toluene, xylene, ethyl acetate, butyl acetate, isopropyl alcohol, styrene, a styrene monomer, methyl ethyl ketone, 2-propanol, dichloromethane, benzene, ethylbenzene, chlorobenzene, paradichlorobenzene, trichloroethylene, acetaldehyde, formaldehyde, and acetone, and is preferably one or more selected from the group consisting of toluene, acetaldehyde, formaldehyde, and acetone. Examples of the article for removing the volatile organic compound include a sheet for removing the volatile organic compound and filters such as a filter for air purification, an air filter, and a chemical filter. In particular, because the activated carbon sheet for air purification according to the present invention has excellent flame retardancy, it can be suitably used especially as an interior material for the passenger compartment of an automobile. Methods of using the activated carbon sheet for air purification according to the present invention include using it as is as a sheet; and using it as an air-purifying filter or an air filter by processing the sheet into a predetermined shape, for example, a honeycomb shape or a corrugated shape, or a molded article obtained by winding the sheet.

A filter according to the present invention comprises a combination of a corrugated sheet and a plane sheet, wherein the corrugated sheet and the plane sheet are a mixed sheet formed of the activated carbon sheet for air purification according to the present invention, and a mass ($g/m^2$) of the activated carbon fiber in the mixed sheet is 5 $g/m^2$ or more.

<Shape and Structure of the Filter>

Figure 1:
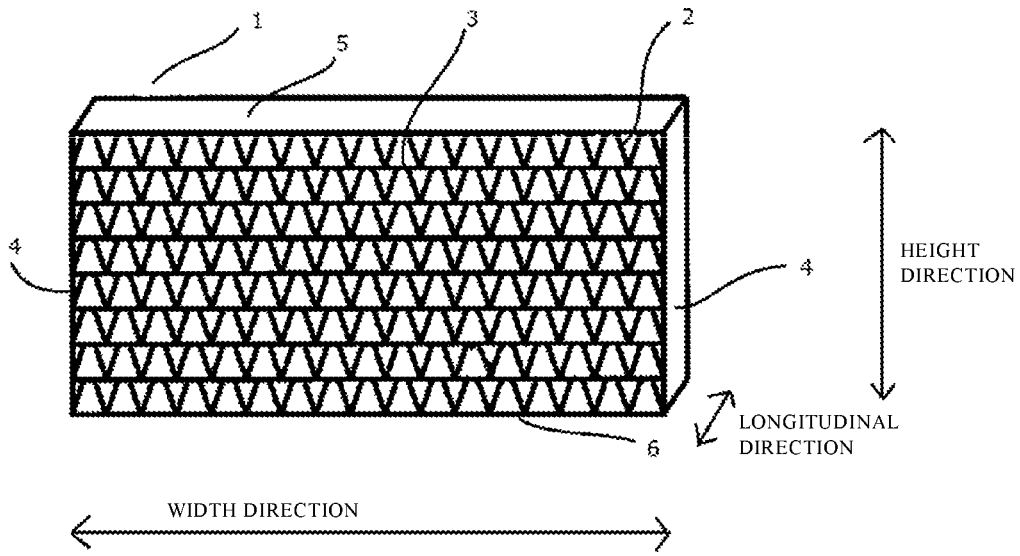
FIG. 1(*a*) is a schematic perspective view showing a filter according to one embodiment of the present invention, and FIG. 1(*b*) is an explanatory diagram of the shape of a pitch (pitch size and pitch height).
Figure 1:
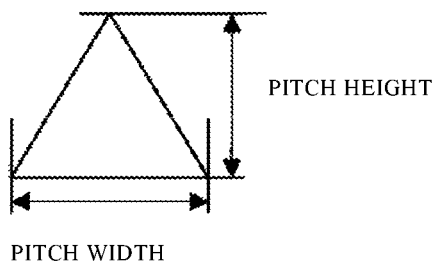

The filter formed of the mixed sheet according to the present invention comprises a combination of a corrugated sheet and a plane sheet. FIG. 1(a) is a schematic perspective view showing a filter according to one embodiment of the present invention. As shown in FIG. 1, a filter 1 according to the present invention comprises a combination of a corrugated sheet 2 and a plane sheet 3. In the embodiment shown in FIG. 1, a plurality of units, each formed of a stack of the corrugated sheet 2 and the plane sheet 3, are stacked. The corrugated sheet 2 can be manufactured by processing the plane sheet using a conventionally known processing method, for example, using a corrugating machine. The corrugated sheet 2 and the plane sheet 3 are then stacked by sequentially bonding them with an adhesive to form the filter according to the present invention. The corrugated sheet 2 and the plane sheet 3 can be bonded by applying, along the ridge line of the corrugated sheet 2, the adhesive over a portion or the overall length of the ridge line.

While the adhesive to be used for stacking the corrugated sheet and the plane sheet is not limited, examples include organic adhesives and inorganic adhesives. Examples of organic adhesives include starch-based, acrylic-based, acryl-styrene-based, vinyl acetate-based, ethylene vinyl acetate copolymer resin-based, and epoxy-based adhesives. Examples of inorganic adhesives include water glass, colloidal silica, calcium silicate, alumina sol, silicone oils, and metal alkoxides.

As shown in FIG. 1, the filter 1 formed of the mixed sheet according to the present invention can include an upper wall 5 and a lower wall 6, and optionally a side wall 4 also. While the side wall 4, the upper wall 5, and the lower wall 6 are not limited, they can be a sheet-shaped material, and are preferably a mixed sheet containing an activated carbon fiber, granular or powdered activated carbon, and a fibrillated fiber, as with the sheet used as the corrugated sheet 2 and the plane sheet 3. The side wall 4, the upper wall 5, or the lower wall 6 can be bonded to the corrugated sheet 2 and/or the plane sheet 3 with an adhesive, for example, as in bonding of the corrugated sheet 2 and the plane sheet 3.

The content of the adhesive relative to the mass of the entire filter is preferably 5 to 30% by mass, and more preferably 10 to 25% by mass, to more satisfactorily achieve filter moldability and toluene adsorption capacity.

FIG. 1(b) is an explanatory diagram of the shape of the pitch (pitch size and pitch height) of the corrugated sheet 2. While the pitch shape of the corrugated sheet 2 is not limited, it is preferably such that the pitch width is 2 to 10 mm and the pitch height is 1 to 6 mm. When the pitch shape is in the above-mentioned range, both toluene adsorption capacity and reduction in the pressure loss of a fluid are more likely to be achieved. Details of the mixed sheet (activated carbon sheet for air purification according to the present invention) that forms the corrugated sheet 2 and the plane sheet 3 are as described above.

EXAMPLES

The present invention will be hereinafter described in detail with reference to examples and comparative examples; however, the present invention is not limited to the examples.

<Preparation of Raw Materials>

(1) Activated Carbon Fibers (1-1) Activated Carbon Fiber A

Granular coal pitch was fed to a melt extruder, where it was melted and mixed at a melting temperature of 320° C., and spun at a discharge rate of 20 g/min to obtain a pitch fiber. The pitch fiber was subjected to an infusiblization treatment by heating for 54 minutes, to 354° C. from ambient temperature in the air at a rate of 1 to 30° C./minute, to obtain an infusiblized pitch fiber as an activated carbon precursor. The activated carbon precursor was activated by conducting a heat treatment at an atmospheric temperature of 875° C. for 30 minutes, while continuously introducing a gas having an $H_2O$ concentration of 100% by volume into an activation furnace, to obtain an activated carbon fiber. The activated carbon fiber had a strength of 0.30 GPa, a specific surface area of 822 $m^2/g$, an average fiber diameter of 16.8 μm, a micropore volume ratio (%) of 96%, a carbon atom content of 90% by mass, and an oxygen atom content of 3% by mass.

(1-2) Activated Carbon Fiber B

Granular coal pitch was fed to a melt extruder, where it was melted and mixed at a melting temperature of 320° C., and spun at a discharge rate of 20 g/min to obtain a pitch fiber. The pitch fiber was subjected to an infusiblization treatment by heating for 54 minutes, to 354° C. from ambient temperature in the air at a rate of 1 to 30° C./minute, to obtain an infusiblized pitch fiber as an activated carbon precursor. The activated carbon precursor was activated by conducting a heat treatment at an atmospheric temperature of 875° C. for 40 minutes, while continuously introducing a gas having an $H_2O$ concentration of 100% by volume into an activation furnace, to obtain an activated carbon fiber. The activated carbon fiber had a strength of 0.25 GPa, a specific surface area of 1277 $m^2/g$, an average fiber diameter of 16.7 μm, a micropore volume ratio (%) of 94%, a carbon atom content of 91% by mass, and an oxygen atom content of 2% by mass.

(2) Granular or Powdered Activated Carbons (2-1) Granular or Powdered Activated Carbon A Powdered activated carbon (trade name HG17-069 manufactured by Osaka Gas Chemicals Co., Ltd., average particle diameter: $D_{50}$=20 μm, specific surface area: 1152 $m^2/g$) having morpholine supported thereon as an aldehyde adsorbent (2-2) Granular or Powdery Activated Carbon B Powdered activated carbon (trade name HG17-067 manufactured by Osaka Gas Chemicals Co., Ltd., average particle diameter: $D_{50}$=20 μm, specific surface area: 712 $m^2/g$) not having an aldehyde adsorbent supported thereon (3) Cellulose-Based Pulp was Used as a Fibrillated Fiber.

(4) Binder Components (4-1) Binder Component A: Polyvinyl Alcohol (4-2) Binder Component B: Trade Name MELTY 4080 Manufactured by UNITIKA LTD.

Example 1

A slurry in which the activated carbon fiber A, the granular or powdered activated carbon A, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 512 $m^2/g$, a basis weight of 101 $g/m^2$, and a thickness of 0.31 mm.

Example 2

A slurry in which the activated carbon fiber A, the granular or powdered activated carbon A, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 519 $m^2/g$, a basis weight of 101 $g/m^2$, and a thickness of 0.32 mm.

Example 3

A slurry in which the activated carbon fiber A, the granular or powdered activated carbons A and B, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 607 m$^2$/g, a basis weight of 98 g/m$^2$, and a thickness of 0.32 mm.

Example 4

A slurry in which the activated carbon fiber A, the granular or powdered activated carbon A, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 505 m$^2$/g, a basis weight of 102 g/m$^2$, and a thickness of 0.33 mm.

Example 5

A slurry in which the activated carbon fiber A, the granular or powdered activated carbon A, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 515 m$^2$/g, a basis weight of 100 g/m$^2$, and a thickness of 0.32 mm.

Example 6

A slurry in which the activated carbon fiber A, the granular or powdered activated carbon B, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 855 m$^2$/g, a basis weight of 100 g/m$^2$, and a thickness of 0.32 mm.

Example 7

A slurry in which the activated carbon fiber A, the granular or powdered activated carbon B, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 913 m$^2$/g, a basis weight of 101 g/m$^2$, and a thickness of 0.31 mm.

Example 8

A slurry in which the activated carbon fiber B, the granular or powdered activated carbon A, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 538 m$^2$/g, a basis weight of 100 g/m$^2$, and a thickness of 0.30 mm.

Example 9

A slurry in which the activated carbon fiber B, the granular or powdered activated carbon A, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to the present invention was obtained. The activated carbon sheet for air purification had a specific surface area of 556 m$^2$/g, a basis weight of 100 g/m$^2$, and a thickness of 0.30 mm.

Example 10

A slurry in which the activated carbon fiber A, the granular or powdered activated carbons A and B, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, a mixed sheet D was obtained. The mixed sheet had a specific surface area of 607 m$^2$/g, a basis weight of 75 g/m$^2$, and a thickness of 0.28 mm.

Comparative Example 1

A slurry in which the granular or powdered activated carbon A, the fibrillated fiber, and the binder component A prepared above were homogeneously dispersed was prepared by mixing them with a pulper to give the mass ratio set forth in Table 1. The slurry was passed onto wires at a predetermined flow rate and dehydrated to adjust the basis weight. The sheet thereafter underwent a press part, a dryer part where the sheet was dried, and a calender part where the sheet surface was smoothened, and then the sheet was wound up onto a reel. As a result, an activated carbon sheet for air purification according to a comparative example was obtained. The activated carbon sheet for air purification had a specific surface area of 498 m$^2$/g, a basis weight of 99 g/m$^2$, and a thickness of 0.31 mm.

Comparative Example 2

A treatment liquid was obtained by adjusting and mixing an aqueous solution of sulfuric acid containing sulfuric acid at a concentration of 75% by mass, p-aminobenzoic acid as an aldehyde adsorbent, and water such that the proportion of sulfuric acid (parts by mass of sulfuric acid alone excluding pure water) was 15 parts by mass, and the proportion of p-aminobenzoic acid was 15 parts by mass, relative to 100 parts by mass of the activated carbon fiber B, and the ratio between the mass of the activated carbon fiber B and the volume of the treatment liquid was 20 g/L. The activated carbon fiber B prepared above was immersed in the treatment liquid for 8 hours and thereafter, the activated carbon fiber was withdrawn from the treatment liquid and dried to obtain the activated carbon fiber B containing p-aminobenzoic acid and sulfuric acid.

The activated carbon fiber B containing p-aminobenzoic acid and sulfuric acid obtained above and the binder component B prepared above were blended to give the mass ratio set forth in Table 1, and the blend was needle-punched to obtain a web. The web was passed through a dryer at 110° C., where the binder component B and the activated carbon fiber were thermally fused. As a result, a sheet according to a comparative example was obtained. The sheet had a specific surface area of 213 m$^2$/g, a basis weight of 50 g/m$^2$, and a thickness of 0.35 mm.

Comparative Example 3

A treatment liquid was obtained by adjusting and mixing an aqueous solution of sulfuric acid containing sulfuric acid at a concentration of 75% by mass, p-aminobenzoic acid as an aldehyde adsorbent, and water such that the proportion of sulfuric acid (parts by mass of sulfuric acid alone excluding pure water) was 15 parts by mass, and the proportion of p-aminobenzoic acid was 15 parts by mass, relative to 100 parts by mass of the activated carbon fiber B, and the ratio between the mass of the activated carbon fiber B and the volume of the treatment liquid was 20 g/L. The activated carbon fiber B prepared above was immersed in the treatment liquid for 8 hours and thereafter, the activated carbon fiber was withdrawn from the treatment liquid and dried to obtain the activated carbon fiber B containing p-aminobenzoic acid and sulfuric acid.

The activated carbon fiber B containing p-aminobenzoic acid obtained above and the binder component B prepared above were blended to give the mass ratio set forth in Table 1, and the blend was needle-punched to obtain a web. The web was passed through a dryer at 110° C., where the binder component B and the activated carbon fiber were thermally fused. As a result, a sheet according to a comparative example was obtained. The sheet had a specific surface area of 501 m$^2$/g, a basis weight of 60 g/m$^2$, and a thickness of 0.40 mm.

<Methods for Measuring Physical Properties of the Activated Carbon Sheets for Air Purification>

(1) Strength, specific surface area, average fiber diameter, micropore volume ratio, carbon atom conten (C content), and oxygen atom content (O content) of the activated carbon fiber: measured and calculated by the above-described methods.

(2) Average particle diameter $D_{50}$ and specific surface area of the granular or powdered activated carbon: measured and calculated by the above-described methods.

(3) Specific surface area, basis weight, and thickness of the activated carbon sheet for air purification: measured and calculated by the above-described methods.

(4) Equilibrium adsorption amount of toluene: measured and calculated by the above-described method. An equilibrium adsorption amount of 2000 mg/m$^2$ or more was determined to be acceptable.

(5) Equilibrium adsorption amount of acetaldehyde: measured and calculated by the above-described method.

(6) Equilibrium adsorption amount of acetone: measured and calculated by the above-described method.

(7) Pressure loss: measured and calculated by the above-described method, more specifically as follows:

(a) Test filter material: a piece of the obtained activated carbon sheet cut in the form of a circle with a diameter of 110 mm was used as a measurement sample.

(b) The apparatus for measuring the pressure loss shown in FIG. 2 was used.

(c) Instruments for measuring the pressure loss were as follows:

1) Duct: a circular one having a structure such that the distribution of air velocity is as flat as possible.

2) Differential pressure gauge: one capable of reading 1 Pa.

3) Holder: one to which the test filter material as specified in (a) above can be mounted, and equipped with a supporting net for protecting the measurement sample.

4) Flow meter: one having the capabilities specified in JIS Z 8761 or JIS Z 8762.

5) Suction pump: one that provides a filtration velocity of 0.1 m/s or more.

The filtration velocity was determined based on the following equation:

$V=Q/A$, where

V: filtration velocity (cm/s);

Q: flow rate (cm$^3$/s) of filtered air; and

A: effective filtration area (cm$^2$) of the test filter material.

(d) Method for measuring the pressure loss: using the apparatus for measuring the pressure loss shown in FIG. 2, air was sucked through the test filter material at a filtration velocity that is an integral multiple of 0.1 m/s, and a difference in static pressure between an upstream side and a downstream side of the test filter material was measured. The pressure loss was calculated based on the following equation:

$\Delta P = P_1 - P_2$, where $\Delta P$: pressure loss (Pa);

$P_1$: static pressure (Pa) at the upstream side of the test filter material; and $P_2$: static pressure (Pa) at the downstream side of the test filter material.

(e) Method for determining the pressure loss: pressure losses for three for more samples of the test filter material were measured, and the average of the measurements was determined as the pressure loss.

(f) Figures up to the one's place of the value determined by the method specified in (e) above were used as significant figures, and determined as the pressure loss in the activated carbon sheet for air purification.

(8) Flame retardancy: five samples cut into a size of 200 mm×50 mm were prepared, and a lighter flame was applied to an end face in the longitudinal direction of each sample. Evaluation was conducted based on the following criteria. ⊚, ○, and Δ were determined to be acceptable.

⊚: In all the five samples, the flame did not spread from the applied place, and the samples self-extinguished.

○: In one or more of the five samples, the flame spread from the applied place, however, all the samples self-extinguished.

Δ: In one or more of the five samples, the flame spread from the applied place, and the samples did not self-extinguish; however, at least one of them self-extinguished.

X: In all the five samples, the flame spread from the applied place, and the samples did not self-extinguish.

(9) Burn distance as measured by the FMVSS 302 burning test: measured in accordance with the FMVSS 302 burning test. A burn distance of 51 mm or less was determined to be acceptable.

(10) Dusting: white adhesive tape was applied to the samples and peeled, and the amounts of coal dust transferred to the tape were visually observed and the degrees were compared.

+: Only a small amount of coal dust transferred to the tape was observed, which was excellent for practical use.

++: An amount of coal dust transferred to the tape was observed, which was not problematic for practical use.

The results are shown in Table 1.

TABLE 1

| | | Ex. 1 | Ex. 2 | Ex. 3 | Ex. 4 | Ex. 5 | Ex. 6 | Ex. 7 | Ex. 8 | Ex. 9 | Ex. 10 | Comp. Ex. 1 | Comp. Ex. 2 | Comp. Ex. 3 |
|---|---|---|---|---|---|---|---|---|---|---|---|---|---|---|
| | Sheet Type | Wet Mixed | Wet Mixed | Wet Mixed | Wet Mixed | Wet Mixed | Wet Mixed | Wet Mixed | Wet Mixed | Wet Mixed | Wet Mixed | Wet Mixed | Dry | Dry |
| Composition (part(s) by mass) | Activated Carbon Fiber A | 10 | 15 | 15 | 5 | 10 | 10 | 15 | 0 | 0 | 15 | 0 | 0 | 0 |
| | Activated Carbon Fiber B | 0 | 0 | 0 | 0 | 0 | 0 | 0 | 10 | 15 | 0 | 0 | 31 | 72 |
| | Granular or Powdered Activated Carbon A | 60 | 55 | 35 | 65 | 60 | 0 | 0 | 60 | 55 | 35 | 70 | 0 | 0 |
| | Granular or Powdered Activated Carbon B | 0 | 0 | 20 | 0 | 0 | 60 | 55 | 0 | 0 | 20 | 0 | 0 | 0 |
| | Fibrillated Fiber | 20 | 20 | 20 | 20 | 25 | 20 | 20 | 20 | 20 | 20 | 20 | 0 | 0 |
| | Binder Component A | 10 | 10 | 10 | 10 | 5 | 10 | 10 | 10 | 10 | 10 | 10 | 0 | 0 |
| | Binder Component B | 0 | 0 | 0 | 0 | 0 | 0 | 0 | 0 | 0 | 0 | 0 | 69 | 28 |
| | Total | 100 | 100 | 100 | 100 | 100 | 100 | 100 | 100 | 100 | 100 | 100 | 100 | 100 |
| Content Ratio between Mass (g/m²) of Activated Carbon Fiber and Mass (g/m²) of Granular or Powdered Activated Carbon (Mass of Activated Carbon Fiber/Mass of Granular or Powdered Activated Carbon) | | 0.17 | 0.27 | 0.27 | 0.08 | 0.17 | 0.17 | 0.27 | 0.17 | 0.27 | 0.27 | 0.00 | Only Activated Carbon Fiber | Only Activated Carbon Fiber |
| Aldehyde Adsorbent Type | | Morpholine | Morpholine | Morpholine | Morpholine | Morpholine | None | None | Morpholine | Morpholine | Morpholine | Morpholine | p-Aminobenzoic Acid | p-Aminobenzoic Acid |
| Mass (g/m²) of Activated Carbon Fiber in Sheet | | 10 | 15 | 15 | 5 | 10 | 10 | 15 | 10 | 15 | 11 | 0 | 16 | 43 |
| Mass (g/m²) of Granular or Powdered Activated Carbon in Sheet | | 61 | 56 | 54 | 66 | 60 | 60 | 56 | 60 | 55 | 41 | 69 | 0 | 0 |
| Specific Surface Area (m²/g) of Sheet | | 512 | 519 | 607 | 505 | 515 | 855 | 913 | 538 | 556 | 607 | 498 | 213 | 501 |
| Basis Weight (g/m²) of Sheet | | 101 | 101 | 98 | 102 | 100 | 100 | 101 | 100 | 100 | 75 | 99 | 50 | 60 |
| Thickness (mm) of Sheet | | 0.31 | 0.32 | 0.32 | 0.33 | 0.32 | 0.32 | 0.31 | 0.30 | 0.30 | 0.28 | 0.31 | 0.35 | 0.40 |
| Toluene Adsorption Capacity (mg/m²) | | 2991 | 2902 | 3739 | 2779 | 2911 | 4950 | 5222 | 3352 | 3250 | 2861 | 2892 | 295 | 1880 |
| Acetaldehyde Adsorption Capacity (mg/m²) | | 444 | 407 | 321 | 452 | 398 | 28 | 29 | 424 | 395 | 246 | 518 | 180 | 390 |
| Acetone Adsorption Capacity (mg/m²) | | 93 | 102 | 151 | 84 | 93 | 239 | 225 | 72 | 78 | 116 | 74 | 11 | 32 |
| Pressure Loss (Pa) at 0.1 m/s | | 50 | 38 | 40 | 70 | 55 | 49 | 39 | 52 | 41 | 31 | 108 | 2 | 3 |
| Flame Retardancy | | ○ | ◎ | ◎ | △ | ++ | ○ | ◎ | ○ | ◎ | ◎ | × | ◎ | ◎ |
| Burn Distance by FMSVSS 302 Burning Test | | 0 mm (did not reach the reference line) | 0 mm (did not reach the reference line) | 0 mm (did not reach the reference line) | 0 mm (did not reach the reference line) | 0 mm (did not reach the reference line) | 0 mm (did not reach the reference line) | 0 mm (did not reach the reference line) | 0 mm (did not reach the reference line) | 0 mm (did not reach the reference line) | 0 mm (did not reach the reference line) | 75 mm | 0 mm (did not reach the reference line) | 0 mm (did not reach the reference line) |
| Dusting | | + | + | + | + | ++ | + | + | + | + | + | + | + | ++ |

As shown in Table 1, the sheets according to Examples 1 to 10 achieved both toluene adsorption capacity and flame retardancy, because they were activated carbon sheets comprising an activated carbon fiber, granular or powdered activated carbon, and a fibrillated fiber, wherein the mass ($g/m^2$) of the activated carbon fiber is 5 $g/m^2$ or more, the pressure loss as measured by the specific method is 150 Pa or less, and the burn distance as measured by the FMVSS 302 burning test is 51 mm or less.

As shown in Table 1, the sheets according to Examples 1 to 5 and 8 to 10 were excellent in toluene adsorption capacity and flame retardancy, and also excellent in acetaldehyde adsorption capacity, because they were wet mixed sheets for air purification comprising an activated carbon fiber, granular or powdered activated carbon, a fibrillated fiber, a binder component, and an aldehyde adsorbent, wherein the mass ($g/m^2$) of the activated carbon fiber is 5 $g/m^2$ or more. Among these sheets, the sheets according to Examples 1 to 3, 5, and 8 to 10 were particularly excellent in flame retardancy because the mass of the activated carbon fiber in the sheet was 9 to 20 $g/m^2$. The sheets according to Examples 1 to 3 and 5 to 10 more satisfactorily achieved both toluene adsorption capacity and flame retardancy, because the content ratio between the mass ($g/m^2$) of the activated carbon fiber and the mass ($g/m^2$) of the granular or powdered activated carbon (mass of the activated carbon fiber/mass of the granular or powdered activated carbon) was 0.15 to 0.30. The sheets according to Examples 1 to 4 and 6 to 10 were superior in dusting inhibition also, because polyvinyl alcohol was used as a binder component, and the proportion of the mass ($g/m^2$) of the binder component relative to a total of 100 parts by mass of the mass ($g/m^2$) of the activated carbon fiber, the mass ($g/m^2$) of the granular or powdered activated carbon, the mass ($g/m^2$) of the fibrillated fiber, and the mass ($g/m^2$) of the binder component was 8 to 13 parts by mass. The sheets according to Examples 1 to 7 and 10 were superior in strength to the sheets according to Comparative Examples 2 and 3, because the strength of the activated carbon fiber was 0.28 GPa or more. The sheets according to Examples 1 to 7 and 10 were also excellent in adsorption amount of acetone, because the activated carbon fiber had a micropore volume ratio of 95% or more.

In contrast, the sheet according to Comparative Example 1 had poor flame retardancy because the mass of the activated carbon fiber was less than 5 $g/m^2$. The sheets according to Comparative Examples 2 and 3 had a poor toluene adsorption capacity because they did not contain granular or powdered activated carbon.

Example 11

Corrugated sheets and plane sheets were prepared using the mixed sheet (activated carbon sheet for air purification) obtained in Example 10. The corrugated sheets were manufactured to have a pitch height of 1.4 mm and a pitch width of 4.2 mm. The corrugated sheets and the plane sheets were stacked alternately as shown in FIG. 1. The corrugated sheets and the plane sheets were bonded with an ethylene vinyl acetate copolymer resin-based adhesive (trade name SP-220N manufactured by Konishi Co., Ltd). The mixed sheet D was used as the upper wall and the lower wall. A filter according to the present invention was thus manufactured. The filter was not provided with a side wall. The filter had a length in the width direction of 200 mm, a length in the longitudinal direction of 10 mm, and a length in the height direction of 120 mm. The adhesive content based on the mass of the entire filter was 24% by mass.

Example 12

A filter according to the present invention was prepared as in Example 11, using the mixed sheet (activated carbon sheet for air purification) obtained in Example 3. The corrugated sheets were manufactured to have a pitch height of 5.0 mm and a pitch width of 8.7 mm. The corrugated sheets and the plane sheets were bonded with a starch-based adhesive. The mixed sheet C was used as the upper wall and the lower wall. A filter according to the present invention was thus manufactured. The filter was not provided with a side wall. The filter had a length in the width direction of 200 mm, a length in the longitudinal direction of 60 mm, and a length in the height direction of 150 mm. The adhesive content based on the mass of the entire filter was 13% by mass.

The following evaluations were conducted on the obtained filters.

(Pressure Loss in Filter)

The filter was cut into a piece whose face parallel to the width direction and height direction was in the form of a circle with a diameter of 100 mm, and whose length in the longitudinal direction of the filter was 10 mm, and the piece was used as a sample. Then, the pressure loss (Pa) in the filter was measured in accordance with JIS B 9927:1999 "Appendix (Standard) Cleanroom—Air filters—Test methods", 3.2 "Pressure Loss Test" as follows: Air was sucked though the sample at a linear velocity of 0.1 m/s in such a manner that the air passed through in the longitudinal direction, and a difference in static pressure between an upstream side and a downstream side of the sample was measured with a differential pressure gauge.

(Flame Retardancy of Filter)

The filter was cut to have a length in the width direction of 100 mm, a length in the longitudinal direction of 10 mm, and a length in the height direction of 100 mm, and a lighter flame was applied to a side in the width direction. Evaluation was conducted based on the following criteria. ○ and Δ were determined to be acceptable.

○: The flame did not spread from the applied place, and the filter self-extinguished.

Δ: Although the flame spread from the applied place, the filter self-extinguished.

X: The flame spread from the applied place, and the filter did not self-extinguish.

(Toluene Removal Capability of Filter)

The filter was cut into a piece whose face parallel to the width direction and height direction was in the form of a circle with a diameter of 15 mm, and whose length in the longitudinal direction of the filter was 20 mm, and into a piece whose face parallel to the width direction and height direction was in the form of a circle with a diameter of 15 mm, and whose length in the longitudinal direction of the filter was 10 mm. These pieces were then stacked in the longitudinal direction such that their circles perfectly fit each other, and fixed from the outside to prevent them from separating. The resulting filter was used as a sample. The sample was set in a glass column with an inner diameter of 15 mm such that the axial direction of the glass column was parallel to the longitudinal direction of the sample, and air containing 2.0 ppm of toluene gas and having a temperature of 25° C. was passed through at an air velocity of 0.5 m/s. Inlet and outlet concentrations in the glass column were measured with an automatic total hydrocarbon analyzer (MODEL-51i manufactured by Nippon Thermo Co., Ltd.), and the toluene gas removal ratio (%) after 30 seconds of passing the air was calculated based on a change in the inlet and outlet concentrations in the glass column to evaluate the toluene removal capability of the filter.

(Acetaldehyde Removal Capability of Filter)

The filter was cut into a piece whose face parallel to the width direction and height direction was in the form of a circle with a diameter of 15 mm, and whose length in the longitudinal direction of the filter was 20 mm, and the piece was used as a sample. The sample was set in a glass column with an inner diameter of 15 mm such that the axial direction of the glass column was parallel to the longitudinal direction of the sample, and air containing 10.0 ppm of toluene gas and having a temperature of 25° C. was passed through at an air velocity of 0.25 m/s. Inlet and outlet concentrations in the glass column were measured by gas chromatography (YX2700-F manufactured by Yanaco Analytical Systems Inc.), and the acetaldehyde gas removal ratio (%) after 30 seconds of passing the air was calculated based on a change in the inlet and outlet concentrations in the glass column to evaluate the acetaldehyde removal capability of the filter.

The results are shown in Table 2.

TABLE 2

|  |  | Ex. 11 | Ex. 12 |
|---|---|---|---|
| Physical Properties of Filter | Pitch Height [mm] | 1.4 | 5 |
|  | Pitch Width [mm] | 4.2 | 8.7 |
|  | Adhesive Used | Ethylene Vinyl Acetate Copolymer Resin-Based | Starch-Based |
|  | Adhesive Content (% by Mass) Based on the Mass of the Entire Filter | 24 | 13 |
| Evaluation Results of Filter Capabilities | Pressure Loss (Pa) at 1 m/s | 3.5 | 0.5 |
|  | Flame Retardancy | ○ | Δ |
|  | Toluene Removal Ratio (%) Acetaldehyde Removal Ratio (%) | 87.7 79.4 | 46.6 23.1 |

The results of Examples 11 and 12 reveal that filters comprising a combination of a corrugated sheet and a plane sheet, wherein the corrugated sheet and the plane sheet are a mixed sheet formed of the activated carbon sheet for air purification according to the present invention, and the mass (g/m$^2$) of the activated carbon fiber in the mixed sheet is 5 g/m$^2$ or more, can achieve both toluene adsorption capacity and flame retardancy.

The invention claimed is:

1. An activated carbon sheet for air purification wherein comprising an activated carbon fiber, granular or powdered activated carbon, and a fibrillated fiber, wherein
   a mass (g/m$^2$) of the activated carbon fiber is 5 g/m$^2$ or more,
   a mass (g/m$^2$) of the granular or powdered activated carbon is 50 g/m$^2$ or more,
   a pressure loss is 150 Pa or less as measurable by cutting a sample of the activated carbon sheet in the form of a circle with a diameter of 110 mm, sucking air through the sample at a linear velocity of 0.1 m/s, measuring a difference in static pressure between an upstream side and a downstream side of the sample using a differential pressure gauge, and rounding the difference to the one's place, and
   a burn distance as measured by the FMVSS 302 burning test is 51 mm or less.

2. The activated carbon sheet for air purification according to claim 1, wherein an equilibrium adsorption amount of toluene at 40° C. and 1 ppm is 2000 mg/m$^2$ or more, and an equilibrium adsorption amount of acetone at 40° C. and 1 ppm is 50 mg/m$^2$ or more.

3. The activated carbon sheet for air purification according to claim 1, wherein a content ratio between the mass (g/m$^2$) of the activated carbon fiber and a mass (g/m$^2$) of the granular or powdered activated carbon (mass of the activated carbon fiber/mass of the granular or powdered activated carbon) is 0.05 to 0.35.

4. The activated carbon sheet for air purification according to claim 1, wherein a content of the activated carbon fiber is 3 to 20% by mass, and
   a content of the granular or powdered activated carbon is 50 to 80% by mass.

5. The activated carbon sheet for air purification according to claim 1, wherein the activated carbon fiber has a tensile strength (GPa) of 0.25 GPa or more.

6. The activated carbon sheet for air purification according to claim 1, wherein the pressure loss is 30 to 50 Pa.

7. An article for removing a volatile organic compound in the air comprising the activated carbon sheet for air purification according to claim 1.

8. An activated carbon sheet for air purification comprising an activated carbon fiber, granular or powdered activated carbon, an aldehyde adsorbent, and a fibrillated fiber, wherein
   the aldehyde adsorbent is supported on the granular or powdered activated carbon, and the aldehyde adsorbent is not supported on the activated carbon fiber,
   a mass (g/m$^2$) of the activated carbon fiber is 5 g/m$^2$ or more,
   a pressure loss is 150 Pa or less as measurable by cutting a sample of the activated carbon sheet in the form of a circle with a diameter of 110 mm, sucking air through the sample at a linear velocity of 0.1 m/s, measuring a difference in static pressure between an upstream side and a downstream side of the sample using a differential pressure gauge, and rounding the difference to the one's place, and
   a burn distance as measured by the FMVSS 302 burning test is 51 mm or less.

9. The activated carbon sheet for air purification according to claim 8, wherein an equilibrium adsorption amount of toluene at 40° C. and 1 ppm is 2000 mg/m$^2$ or more, and an equilibrium adsorption amount of acetone at 40° C. and 1 ppm is 50 mg/m$^2$ or more.

10. The activated carbon sheet for air purification according to claim 8, wherein a content ratio between the mass (g/m$^2$) of the activated carbon fiber and a mass (g/m$^2$) of the granular or powdered activated carbon (mass of the activated carbon fiber/mass of the granular or powdered activated carbon) is 0.05 to 0.35.

11. The activated carbon sheet for air purification according to claim 8, wherein a content of the activated carbon fiber is 3 to 20% by mass, and
    a content of the granular or powdered activated carbon is 50 to 80% by mass.

12. The activated carbon sheet for air purification according to claim 8, wherein the activated carbon fiber has a tensile strength (GPa) of 0.25 GPa or more.

13. The activated carbon sheet for air purification according to claim 8, wherein the pressure loss is 30 to 50 Pa.

14. An article for removing a volatile organic compound in the air comprising the activated carbon sheet for air purification according to claim 8.

* * * * *